(12) United States Patent
Holmgren et al.

(10) Patent No.: US 6,383,967 B1
(45) Date of Patent: May 7, 2002

(54) SELECTIVE AROMATICS DISPROPORTIONATION/ TRANSALKYLATION CATALYST

(75) Inventors: Jennifer S. Holmgren, Bloomingdale; Douglas B. Galloway, Mount Prospect; Leonid B. Galperin, Wilmette; Richard R. Willis, Cary, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/431,857

(22) Filed: Nov. 2, 1999

Related U.S. Application Data

(63) Continuation-in-part of application No. 08/986,385, filed on Dec. 8, 1997, now Pat. No. 6,008,423.

(51) Int. Cl.[7] .......................... B01J 29/06; B01J 29/04; B01J 21/00
(52) U.S. Cl. .............................. 502/64; 502/61; 502/63; 502/73
(58) Field of Search ............................. 502/60, 61, 63, 502/64, 71, 73, 77, 87; 585/475; 423/DIG. 22, DIG. 33, DIG. 29, DIG. 35

(56) References Cited

U.S. PATENT DOCUMENTS

| | | | |
|---|---|---|---|
| 4,097,543 A | 6/1978 | Haag et al. ................. 260/672 |
| 4,276,437 A | 6/1981 | Chu ........................... 585/467 |
| 4,414,138 A | * 11/1983 | Petty et al. .................... 502/73 |
| 4,418,006 A | * 11/1983 | Kim et al. ...................... 502/73 |
| 4,487,843 A | * 12/1984 | Telford et al. ................. 502/85 |
| 4,670,412 A | * 6/1987 | Chang et al. .................. 502/77 |
| 4,724,066 A | 2/1988 | Kirker et al. ................ 208/114 |
| 4,913,796 A | * 4/1990 | Valyocsik ..................... 208/46 |
| 4,922,055 A | 5/1990 | Chu ........................... 585/470 |
| 4,968,650 A | * 11/1990 | Chu et al. ...................... 502/61 |
| 5,034,363 A | 7/1991 | Petit et al. ..................... 502/61 |
| 5,041,401 A | * 8/1991 | Schoennagel et al. ......... 502/61 |
| 5,244,852 A | * 9/1993 | Lachman et al. .............. 502/66 |
| 5,292,991 A | * 3/1994 | Lachman et al. ............. 585/850 |
| 5,463,155 A | * 10/1995 | Galperin et al. ............. 585/310 |
| 5,472,593 A | * 12/1995 | Gosling et al. ................ 208/65 |
| 5,498,810 A | * 3/1996 | Bogdan et al. .............. 585/310 |
| 5,762,902 A | * 6/1998 | Benazzi et al. ............... 423/700 |
| 5,792,338 A | * 8/1998 | Gosling et al. ................ 208/65 |
| 5,831,139 A | * 11/1998 | Schmidt et al. .............. 585/315 |
| 5,898,090 A | * 4/1999 | Hammerman et al. ....... 585/477 |
| 6,008,425 A | * 12/1999 | Mohr et al. .................. 585/481 |
| 6,063,975 A | * 5/2000 | Drake et al. ................. 585/418 |

* cited by examiner

Primary Examiner—Steven P. Griffin
Assistant Examiner—Cam N. Nguyen
(74) Attorney, Agent, or Firm—John G. Tolomei; John F. Spears, Jr.; Thomas K. McBride, Jr.

(57) ABSTRACT

A zeolitic catalyst useful in the selective disproportionation and transalkylation of toluene comprises a molecular sieve having a pore diameter of about 5 to 8 Å, a refractory inorganic oxide and a reduced weak non-framework metal which is believed to provide Lewis acidity.

7 Claims, 3 Drawing Sheets

US 6,383,967 B1

SELECTIVE AROMATICS DISPROPORTIONATION/ TRANSALKYLATION CATALYST

CROSS REFERENCE TO RELATED APPLICATION

This application is a Continuation-in-Part of prior U.S. application Ser. No. 08/986,385 filed Dec. 8, 1997, U.S. Pat. No. 6,008,423, issued Dec. 28, 1999.

BACKGROUND OF THE INVENTION

This invention relates to an improved process for the conversion of aromatic hydrocarbons. More specifically, the invention concerns disproportionation and transalkylation of aromatic hydrocarbons to obtain xylenes.

The xylene isomers are produced in large volumes from petroleum as feedstocks for a variety of important industrial chemicals. The most important of the xylene isomers is paraxylene, the principal feedstock for polyester which continues to enjoy a high growth rate from large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Most commonly, toluene is dealkylated to produce benzene or disproportionated to yield benzene and $C_8$ aromatics from which the individual xylene isomers are recovered. More recently, processes have been introduced to disproportionate toluene selectively to obtain higher-than-equilibrium yields of paraxylene.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market. A higher yield of xylenes at the expense of benzene thus is a favorable objective, and processes to transalkylate $C_9$ aromatics along with toluene have been commercialized to obtain high xylene yields.

U.S. Pat. No. 4,097,543 (Haag et al.) teaches toluene disproportionation for the selective production of paraxylene using a zeolite having a silica/alumina ratio of at least 12 and a constraint index of 1 to 12, which zeolite has undergone controlled precoking. The zeolite may be ion-exchanged with a variety of elements from Group IB to VIII, and composited with a variety of clays and other porous matrix materials.

U.S. Pat. No. 4,276,437 (Chu) teaches transalkylation and disproportionation of alkylaromatics to yield predominantly the 1,4-alkylaromatic isomer using a zeolite which has been modified by treatment with a compound of a Group IIIB element. The catalyst optionally contains phosphorus, and it is contemplated that the Group IIIB metal is present in the oxidized state.

U.S. Pat. No. 4,922,055 (Chu) teaches toluene disproportionation using a zeolite, preferably ZSM-5, containing framework gallium, shown to be superior to non-framework gallium. Selective production of paraxylene is not disclosed in this reference.

The accepted mechanism for transalkylation and disproportionation is believed to be effected via a strong Brönsted acid such as is provided by a zeolitic aluminosilicate. A lower-energy path, however, would provide potential for greater selectivity and improved economics.

U.S. Pat. No. 4,724,066 (Kirker et al.) describes a catalyst for toluene disproportionation containing a zeolite such as ZSM-5 or Beta and a microcrystalline, microporous aluminum phosphate component. The reference describes incorporation of optional metal components described as a "difficultly reducible oxide" or an optional hydrogenation component. Both optional components may be chosen from a very long list of elements, with the hydrogenation component list including rhenium.

SUMMARY OF THE INVENTION

It is an object of the present invention to provide an improved catalyst for the disproportionation and/or transalkylation of aromatic hydrocarbons to yield desirable alkylaromatic isomers. A specific objective is obtain a high yield of paraxylene by disproportionation of toluene, or transalkylation of toluene and higher aromatics.

This invention is based on the discovery that high activity with potential for selectivity to paraxylene is obtained by disproportionation of toluene using a zeolitic catalyst containing a reduced weak metal.

A broad embodiment of the present invention is directed to a process for the disproportionation of a toluene feedstock to obtain a product comprising paraxylene using a catalyst comprising a molecular sieve having a pore diameter of from about 5 to 8 Å, an elective refractory inorganic oxide and a reduced weak metal. Optionally, the feedstock comprises $C_9$ aromatics which are disproportionated to yield additional $C_8$ aromatics. The catalyst preferably is subjected to a conditioning step prior to its use for disproportionation/transalkylation in order to deposit a controlled concentration of carbon on the catalyst and increase its selectivity to paraxylene in the product.

The catalyst of the present invention comprises a zeolitic aluminosilicate preferably selected from MFI, MEL, MTW and TON, and most preferably comprises MFI. The optional refractory inorganic oxide preferably comprises one or both of alumina and silica, and an amorphous aluminum phosphate binder is favored. The catalyst also contains a non-framework weak metal. The weak metal is defined by its ability to effect $H_2/D_2$ exchange without effecting methylcyclohexane dehydrogenation at 300°–500° C. The metal is preferably selected from the group consisting of Ga, Re and Bi and optimally is selected from gallium and bismuth.

A process combination employing the subject process optionally comprises a xylene-separation zone in which paraxylene is recovered by adsorption.

These, as well as other objects and embodiments, will become apparent from the detailed description of the invention.

DESCRIPTION OF THE PREFERRED EMBODIMENTS

Figure 1:
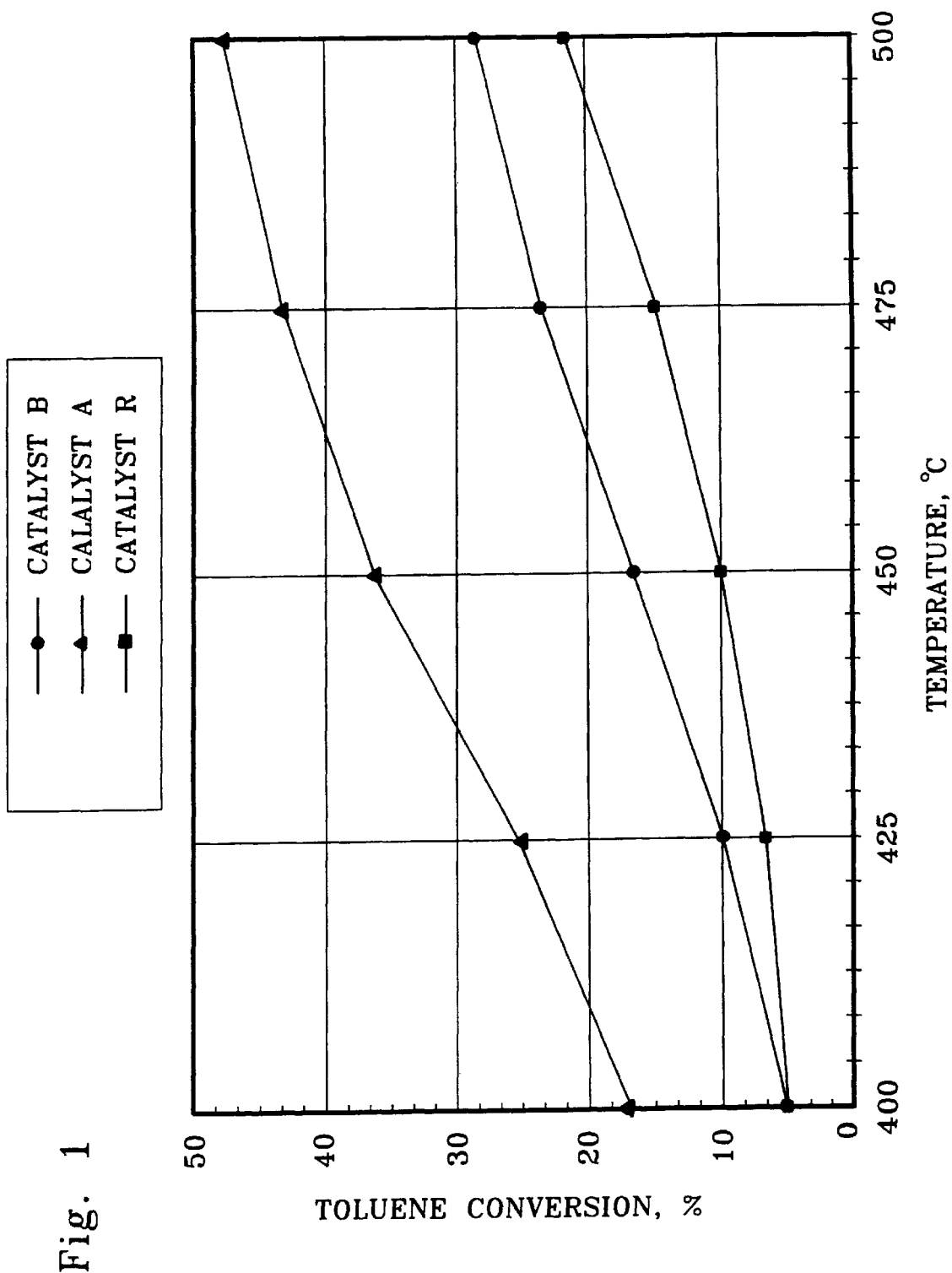
FIG. 1 shows toluene conversion in a transalkylation reaction as a function of temperature.

A broad embodiment of the present invention is directed to the disproportionation of a toluene feedstock to obtain a product comprising paraxylene using a catalyst comprising a molecular sieve having a pore diameter of from about 5 to 8 Å, a refractory inorganic oxide and a reduced weak metal. Other embodiments of the invention encompass but are not limited to parameters such as incremental and alternative feedstocks, catalyst composition and operating conditions.

The feedstock to the subject process contains toluene and suitably is derived from one or a variety of sources. Toluene may be produced synthetically for example, from naphtha by catalytic reforming or by pyrolysis followed by hydrotreating to yield an aromatics-rich product. The toluene feedstock may be derived from such product with suitable purity by extraction of aromatic hydrocarbons from a mixture of aromatic and nonaromatic hydrocarbons and fractionation of the extract. Large quantities of aromatic hydrocarbons are recovered in this way commercially. For instance, aromatics may be recovered from a reformate through the use of a selective solvent, such as one of the sulfolane type, in a liquid-liquid extraction zone. The recovered aromatics may then be separated into streams having the desired carbon number range by fractionation. The feedstock should contain no more than about 10 mass-% nonaromatics; the content of benzene and $C_8$ aromatics is principally an economic decision relating to the efficiency of conversion of toluene to these aromatics. When the severity of reforming or pyrolysis is sufficiently high, extraction may be unnecessary and fractionation may be sufficient to prepare the toluene feedstock.

The toluene feedstock, usually in admixture with toluene recycled from the products of the disproportionation reaction, is preferably admixed with hydrogen to effect a combined feed to a disproportionation zone. If present, the hydrogen need not exceed a 20:1 mole ratio to hydrocarbons to effect satisfactory stability in the disproportionation reaction, and preferably is in the range of from about 0.5 to 10 mole ratio. The hydrogen may contain hydrocarbons, such as methane and ethane, and inerts such as nitrogen, but preferably is in a concentration of at least about 90 mole-% to avoid large hydrogen losses and unfavorable process economics. The disproportionation reaction yields a paraxylene-containing product which usually also comprises benzene, other $C_8$ aromatics, and smaller amounts of $C_9$+ aromatics.

An optional component of the combined feed when transalkylation is an objective of the process is a heavy-aromatics stream comprising $C_9$ aromatics, thereby effecting transalkylation of toluene and $C_9$ aromatics to yield additional Xylenes. Indane may be present in the heavy-aromatics stream although it is not a desirable component to effect high yields of $C_8$-aromatics product. $C_{10}$ aromatics also may be present, preferably in an amount of 30% or less of the feed. The heavy-aromatics stream preferably comprises at least about 90 mass-% aromatics, and may be derived from the same or different known refinery and petrochemical processes as the toluene feedstock and/or may be recycled from the separation of the product from disproportionation/transalkylation. Benzene also may be present in the combined feed to disproportionation/transalkylation.

The combined feed to the disproportionation zone usually is first heated by indirect heat exchange against the effluent of the reaction zone and is then further heated in a fired heater. The vaporous stream is then passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of a vaporous effluent stream comprising hydrogen and both the feed and product hydrocarbons. This effluent is normally cooled by indirect heat exchange against the stream entering the reaction zone and then further cooled through the use of air or cooling water. The temperature of the effluent stream is normally lowered sufficiently to effect the condensation of substantially all of the feed and product hydrocarbons having six or more carbon atoms per molecule. The resultant mixed-phase stream is passed into a vapor-liquid separator wherein the two phases are separated and from which the hydrogen-rich vapor is recycled to the reaction zone. The condensate from the separator is passed into a stripping column in which substantially all $C_5$ and lighter hydrocarbons present in the effluent are concentrated into an overhead stream and removed from the process. An aromatics-rich stream is recovered as net stripper bottoms which is referred to herein as the disproportionation effluent stream.

Conditions employed in the disproportionation zone of the subject process normally include a temperature of from about 200° to 600° C., and preferably from about 350° to 575° C. The temperature required to maintain the desired degree of conversion will increase as the catalyst gradually loses activity during processing. Normal end-of-run temperatures may therefore exceed start-of-run temperatures by 65° C. or more. In the transalkylation embodiment wherein toluene and $C_9$ aromatics are present in the combined feed, reaction temperatures generally are somewhat lower within the range of about 200° to 525° C.

The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of paraxylene at the expense of conversion. Liquid hourly space velocities generally are the range of from about 0.2 to 10 $hr^{-1}$, with a value in the range of from 0.8 to 3 $hr^{-1}$ being preferred.

The disproportionation effluent stream is separated into a light recycle stream, a mixed $C_8$ aromatics product and a heavy-aromatics stream. The $C_8$ aromatics product may be sent to a xylene separation zone for recovery of pure paraxylene and/or, optionally, other xylenes and ethylbenzene. The light recycle stream may be diverted to other uses such as to benzene and toluene recovery, but alternatively is recycled partially to the disproportionation zone since it contains not only benzene and toluene but also amounts of nonaromatics which would remain with the benzene and reduce its commercial value. The heavy recycle stream contains substantially all of the $C_9$ and heavier aromatics and may be partially or totally recycled to the reaction if transalkylation is an objective of the process.

The xylene-separation zone may use any one or several different separation techniques such as fractionation, crystallization or selective adsorption to remove paraxylene from the stream of mixed $C_8$ aromatics which enters the xylene-separation zone. An adsorptive separation zone is preferred containing a bed of molecular sieves operated in accordance with the teaching of U.S. Pat. No. 3,201,491 to simulate the use of a continuously moving bed of molecular sieves. Subsequent improvements to the process are described in U.S. Pat. Nos. 3,696,107 and 3,626,020. The preferred xylene-separation zone is therefore operated at adsorption conditions which include temperatures in the range of from about 30° to 300° C., but preferably from 40° to 250° C. This zone may be operated in either the vapor phase or the liquid phase with liquid-phase operations being preferred. Pressures utilized may vary from atmospheric to 70 atmospheres, with more moderate pressures of from about 5 to 20 atmospheres being preferred. Further details on the operation of the preferred xylene-separation zone may also be obtained from U.S. Pat. Nos. 4,039,599 and 4,184, 943 and the previously cited references which concern paraxylene separation. The xylene-separation zone may depart from this preferred mode of operation through the use of batch-type operations or a true moving bed of solid adsorbent. The simulated cocurrent adsorptive separation process of U.S. Pat. No. 4,402,832 may also be employed. The extract and raffinate streams may be handled as described in these references or as described in U.S. Pat. No. 4,381,419.

The skilled routineer will recognize variations in the process combination described above which are within the scope of the invention. For example, benzene as well as toluene may be charged to the disproportionation zone as a supplementary feedstock. The xylene-separation zone may use one or more of several known separation techniques such as adsorption, crystallization and fractionation. Orthoxylene and/or metaxylene may be recovered as pure products from the xylene-separation zone.

The catalyst of the present invention comprises a molecular sieve, a refractory inorganic oxide, and a reduced nonframework weak metal. The preferred molecular sieves are zeolitic aluminosilicates which may be any of those which have a Si:Al$_2$ ratio greater than about 10, preferably greater than 20, and a pore diameter of about 5 to 8 Angstroms (Å). Specific examples of zeolites which can be used are the MFI, MEL, EUO, FER, MFS, MTT, MTW, TON, MOR and FAU types of zeolites. MFI, MEL, MTW and TON are preferred, and MFI-type zeolites, also often designated ZSM-5, are especially preferred.

The preparation of the preferred MFI-type zeolites is well known in the art. The zeolites generally are prepared by crystallizing a mixture containing an alumina source, a silica source, an alkali metal source, water and a tetraalkyl ammonium compound or its precursor. The amount of zeolite present in the catalyst can vary considerably but usually is present in an amount from about 30 to 90 mass percent and preferably from about 50 to 70 mass percent of the catalyst.

A refractory binder or matrix preferably is utilized to facilitate fabrication of the disproportionation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, zinc oxide and silica. Alumina and/or silica are preferred binders.

One suitable example of a binder or matrix component is a preferably amorphous phosphorus-containing alumina (hereinafter referred to as aluminum phosphate) component. The phosphorus may be incorporated with the alumina in any acceptable manner known in the art. One preferred method of preparing this aluminum phosphate is that described in U.S. Pat. No. 4,629,717 which is incorporated by reference. The technique described in the '717 patent involves the gellation of a hydrosol of alumina which contains a phosphorus compound using the well-known oil drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to 1.5:1 mass ratio. A phosphorus compound is now added to the sol. Preferred phosphorus compounds are phosphoric acid, phosphorous acid and ammonium phosphate. The relative amount of phosphorus and aluminum expressed in molar ratios ranges from about 1:1 to 1:100 on an elemental basis. The resulting aluminum phosphate hydrosol mixture then is gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours. The amount of phosphorus-containing alumina component present (as the oxide) in the catalyst can range from about 10 to 70 mass percent and preferably from about 30 to 50 mass percent.

The zeolite and aluminum phosphate binder are mixed and formed into particles by means well known in the art such as gellation, pilling, nodulizing, marumerizing, spray drying, extrusion or any combination of these techniques. A preferred method of preparing the zeolite/aluminum phosphate support involves adding the zeolite either to an alumina sol or a phosphorus compound, forming a mixture of the alumina sol/zeolite/phosphorus compound which is now formed into particles by employing the oil drop method described above. The particles are calcined as described above to provide a support for the metal component.

Another essential component of the instant catalyst is a weak non-framework metal. The metal is present in the finished catalyst primarily in a reduced state, i.e. over about 50% of the metal, preferably at least about 75%, and more preferably at least about 90%, of the metal is present in the catalyst in an oxidation state of less than +3. It is believed, without limiting the invention, that some of the metal is present in the catalyst at an oxidation state between +3 and the elemental metal, and that this metal acts as a Lewis acid in the disclosed reactions. The weak metal promotes $H_2/D_2$ exchange without effecting methylcyclohexane dehydrogenation at a temperature of between about 300° and 500° C. Preferably the metal is selected from the group consisting of gallium, rhenium and bismuth, more preferably consists essentially of either gallium or bismuth, and most preferably consists essentially of gallium.

In the preferred preparation of the catalyst, a gallium or bismuth component may be deposited onto the support in any suitable manner to effect the disclosed characteristics of the instant catalyst. A gallium component suitably is deposited onto the support by impregnating the support with a salt of the gallium metal. The particles are impregnated with a gallium salt selected from the group consisting of gallium nitrate, gallium chloride, gallium bromide, gallium hydroxide, gallium acetate, and the like. Suitable bismuth salts comprise, for example, bismuth nitrate, bismuth acetate, bismuth trichloride, bismuth tribromide, and bismuth trioxide. It is believed, without so limiting the invention, that the gallium and/or bismuth is more concentrated on the binder than on the zeolite component of the catalyst. Hence, the metal is referred to as non-framework metal. The amount of gallium, rhenium and/or bismuth which is deposited onto the support varies from about 0.1 to 5 mass percent of the finished catalyst, expressed as the elemental metal.

The gallium and/or bismuth component may be impregnated onto the support particles by any technique well known in the art such as dipping the catalyst into a solution of the metal compound or spraying the solution onto the support. One preferred method of preparation involves the use of a steam jacketed rotary dryer. The support particles are immersed in the impregnating solution contained in the dryer and the support particles are tumbled therein by the rotating motion of the dryer. Evaporation of the solution in contact with the tumbling support is expedited by applying steam to the dryer jacket. After the particles are completely dry, they are heated under a hydrogen atmosphere at a temperature of about 500 to 700° C. for a time of about 1 to 15 hours. Although a pure hydrogen atmosphere is preferred to reduce and disperse the metal, the hydrogen may be diluted with nitrogen. Alternatively, it is envisioned that the reduction and dispersion can be done in situ in the actual reactor vessel used for dehydrocyclodimerization by using either pure hydrogen or a mixture of hydrogen and hydrocarbons. Next the hydrogen treated particles are heated in air and steam at a temperature of about 400 to 700° C. for a time of about 1 to 10 hours. The amount of steam present in the air varies from about 1 to 40 percent.

In one embodiment the catalyst particles, which preferably contain well dispersed gallium present as gallium oxide, optionally may be treated with an aqueous solution of a weakly acidic ammonium salt or a dilute acid solution. The ammonium salts which can be used include ammonium chloride, ammonium acetate and ammonium nitrate. The concentration of these salts can vary from about 0.1 to 5 molar. The acids which can be used include hydrochloric, acetic, nitric and sulfuric acid. Although concentrated acids may be used, they would degrade the zeolite and the integrity of the particles, as well as removing the undesirable aluminum phosphorus species. Thus, it is desirable to use dilute acids which have a molarity from about 0.1 to 5 moles/liter. Of these treatment solutions, it is preferred to use an ammonium nitrate solution. The treating solution is contacted with the calcined catalyst particles at a temperature of about 50° to 100° C. for a time of about 1 to 48 hours and the particles are separated from the aqueous solution.

To provide the finished catalyst, the catalyst particles are dried and calcined at a temperature of about 500 to 700° C. for a time of about 1 to 15 hours.

Optionally, the catalyst may be subjected to precoking in order to increase the proportion of paraxylene in the $C_8$ aromatics product. The precoking will increase the carbon on a previously used regenerated catalyst and should produce a catalyst which comprises between about 10 and 30 mass-% carbon as proportion of the catalyst. Precoking of the present catalyst effects a proportion of paraxylene in the product above equilibrium levels at disproportionation conditions, preferably at least about 80 mass-% and optimally about 90 mass-% or more of the $C_8$ aromatics. Precoking is effected on fresh or regenerated catalyst prior to its use for disproportionation usually at one or more of a higher temperature, lower space velocity, and lower hydrogen-to-hydrocarbon ratio relative to the disproportionation conditions. Such operating conditions generally are within the ranges of those disclosed before for disproportionation, with operating temperature trending toward the upper end of the range. Precoking time ranges from about 0.5 hours to 10 days. The feedstock as described herein may be used for precoking, or other specific hydrocarbons or mixtures preferably comprising aromatics may be used. Further details relative to precoking are disclosed in U.S. Pat. No. 4,097,543, incorporated herein by reference.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

An aluminum-phosphate-bound MFI catalyst was prepared as a control to illustrate a disproportionation process not of the invention. A first solution was prepared by adding phosphoric acid to an aqueous solution of hexamethylenetetraamine (HMT) in an amount to yield a phosphorus content of the finished catalyst equal to about 11 weight percent. A second solution was prepared by adding an MFI-type zeolite having an $Si/Al_2$ ratio of about 38 to enough alumina sol, prepared by digesting metallic aluminum in hydrochloric acid, to yield a zeolite content in the finished catalyst equal to about 67 weight percent. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres. The spheres were removed from the oil bath, water washed, air dried, and calcined at a temperature of about 482° C. This control catalyst, to be used to provide reference disproportionation results, was identified as Catalyst R.

Example II

A catalyst was prepared to illustrate the disproportionation process of the invention. A solution of gallium nitrate was utilized to impregnate the spheres of Catalyst R to achieve a gallium content on the finished catalyst equal to about 1 mass percent. After impregnation, the spheres were dried, heated in pure hydrogen at 580° C. for 6 hours, and finally calcined in the presence of steam at a temperature of about 650° C. This catalyst was identified as Catalyst A and contained 1.0 mass-% gallium as the elemental metal.

Example III

Catalysts R and A were tested for comparative activity and selectivity in toluene disproportionation. The feedstock was substantially pure toluene as derived from solvent extraction, with a purity of about 99.9 mass-%. Operating conditions comprised a pressure of about 2.8 MPa, weight hourly space velocity of 2.0 $hr^{-1}$ and temperatures varying in a pattern of 25° increments from 400° to 500° C.

Catalyst A after completion of the test was recovered as spent catalyst and designated Catalyst B. Catalyst B then was tested with the same feedstock and same conditions as reported above for Catalysts R and A.

Figure 2:
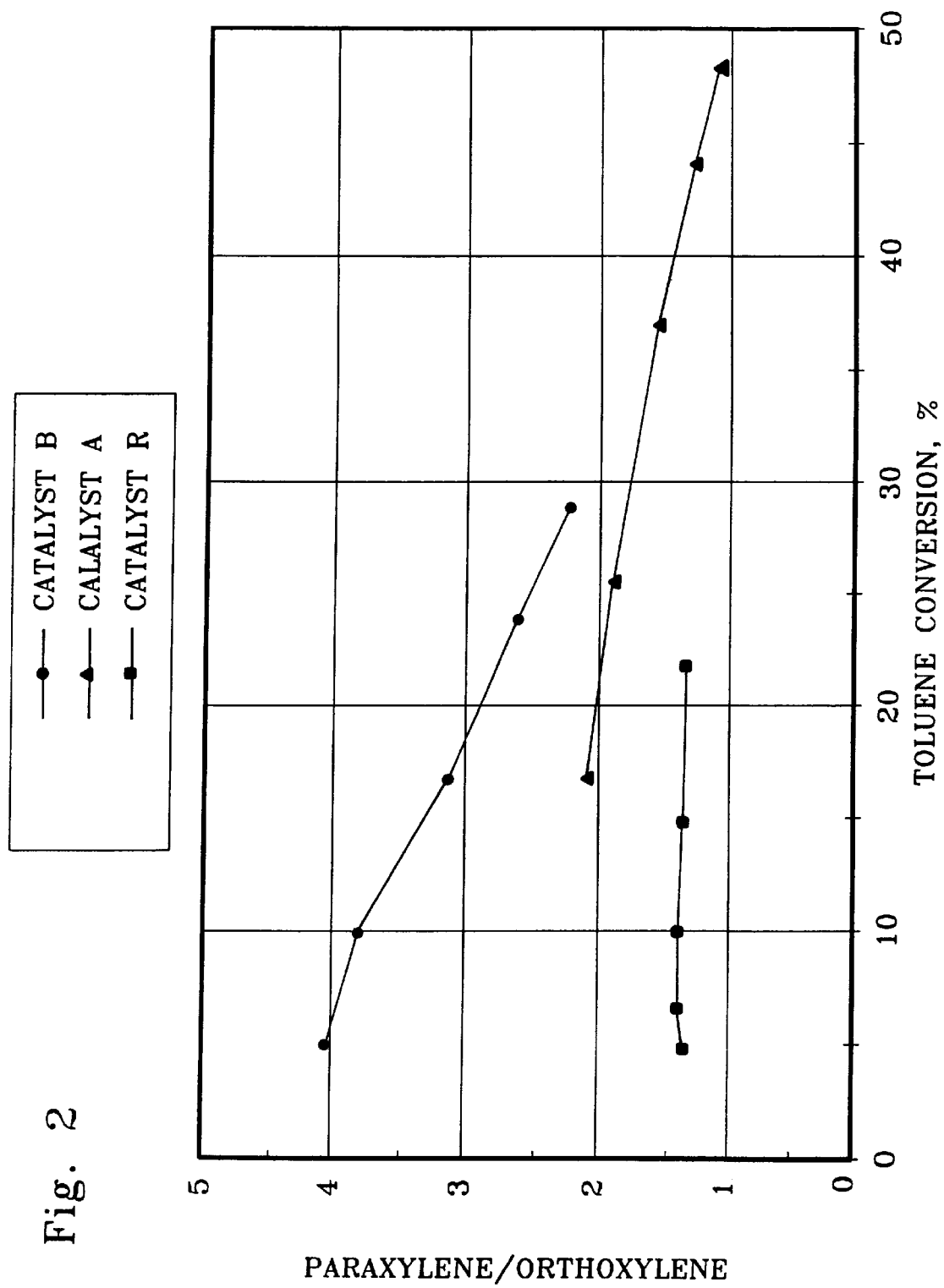
FIG. 2 shows selectivity to paraxylene as product paraxylene/orthoxylene ratio as a function of toluene conversion.

The results of the tests are shown in FIGS. 1 and 2. FIG. 1 is a plot of activity, expressed as toluene conversion, vs. conversion temperature. Catalyst A demonstrated significantly higher activity than Catalyst R; Catalyst B was substantially less active than Catalyst A, but still showed an advantage over Catalyst R.

FIG. 2 is a plot of selectivity, expressed as the mass ratio of paraxylene to orthoxylene in the product, vs. toluene conversion. Again, both Catalysts A and B showed a significant advantage over the control Catalyst R. By this standard, however, spent Catalyst B showed a selectivity advantage over Catalyst A.

Example IV

A bismuth-containing bound-zeolite catalyst of the invention was prepared by the method described in Example II. A solution of bismuth nitrate was utilized to impregnate the spheres of Catalyst R to achieve a bismuth content on the finished catalyst equal to about 3 mass percent. After impregnation, the spheres were dried, heated in pure hydrogen at 580° C. for 6 hours, and finally calcined in the presence of steam at a temperature of about 650° C. This catalyst was identified as Catalyst C and contained 2.9 mass-% bismuth as the elemental metal.

Example V

Tin- and indium-containing bound-zeolite catalysts not of the invention were prepared by the method described in Example II. After impregnation of the respective metal components in the spheres of Catalyst R, the spheres were dried, heated in pure hydrogen, and calcined in the presence of steam. These catalysts were identified respectively as Catalysts S and T and had the following metals contents expressed as mass-% of the elemental metal:

| | |
|---|---|
| Catalyst S | 1.7% Sn |
| Catalyst T | 1.6% In |

Example VI

Metals-containing unbound-zeolite catalysts of the invention were prepared by impregnating MFI-type zeolite with compounds of gallium, bismuth and rhenium. After impregnation of the respective metal components, the zeolites were dried and calcined. These catalysts were identified respectively as Catalysts D, E and F and had the following metals contents expressed as mass-% of the elemental metal:

| | |
|---|---|
| Catalyst D | 1.0% Ga |
| Catalyst E | 2.9% Bi |
| Catalyst F | 1.0% Re |

Example VII

Various catalysts of the invention and not of the invention as described hereinabove, along with the MFI-type zeolite having the absence of metals, were tested for disproportionation activity. An atmospheric microreactor was used to test activity, based on conversion of toluene at 500° C. Results were as follows, expressing conversion as % of toluene feedstock:

| Catalyst | Invention | Not Invention |
|---|---|---|
| A | 35.8 | |
| C | 38.6 | |
| D | 40.3 | |
| E | 44.5 | |
| R | | 9.9 |
| S | | 10.7 |
| T | | 10.7 |
| MFI | | 13.3 |

Example VIII

Catalysts of the invention and not of the invention were compared for ability to dehydrogenate methylcyclohexane to toluene, in which a higher value would represent reduced selectivity for the disproportionation reaction measured in Example VII. In addition to catalysts described hereinabove, the following were tested:

Catalyst F: Rhenium on MFI zeolite

Catalyst X: Aluminum phosphate prepared per Example I ex zeolite

Catalyst Y: Catalyst X containing tin

Catalyst Z: Catalyst X containing platinum and tin

The dehydrogenation was effected in an atmospheric reactor at two alternative temperatures, 350° and 500° C., with results reported as mass-% of methylcyclohexane converted to toluene:

| Catalyst | 350° C. | 500° C. |
|---|---|---|
| D (invention) | 0.1 | 7.8 |
| E (invention) | 0 | 5.9 |
| F (invention) | 0.2 | 1.3 |
| X (not invention) | 0 | 2.5 |
| Y (not invention) | 0.4 | — |
| Z (not invention) | 40.1 | 66.9 |

Dehydrogenation activity of catalysts of the invention containing gallium, bismuth or rhenium was very low, comparable to catalysts not of the invention and in contrast to the Pt—Sn-containing catalyst having dehydrogenation activity as known in the art.

Example IX

Catalysts of the invention and not of the invention were reviewed for their capability to effect deuterium-hydrogen exchange. Powder samples were pressed into 13 mm self-supporting pellets and pretreated in flowing helium at 550° C. for one hour. The samples were cooled to room temperature and a spectrum recorded for hydroxyl analysis. Deuterium exchange was effected by injecting a 10 cc aliquot of $D_2$, equilibrating for four minutes, and ramping temperature to 500° C. at 5° C./minute. The excess deuterium then was purged for three minutes and the sample was cooled to room temperature for recording of a final spectrum.

Figure 3:
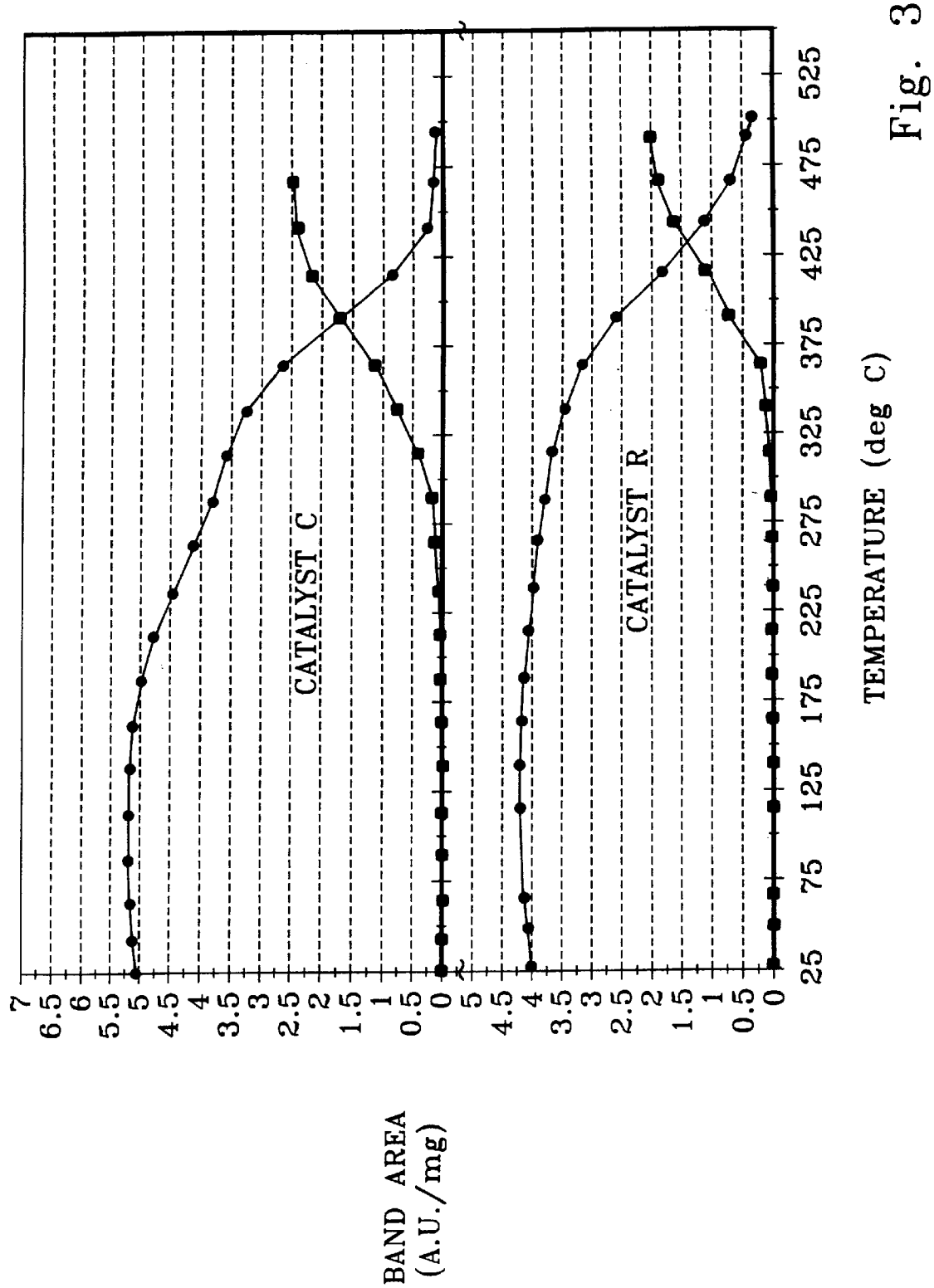
FIG. 3 shows integrated areas of —OH and —OD absorbance bands in deuterium exchange as a function of temperature.

The deuterium-exchange capability of bismuth-containing Catalyst C of the invention was compared to that of the control Catalyst R, plotting the integrated areas of normalized —OH and —OD absorbance bands over a range of temperatures. The plot is shown as FIG. 3, and shows a difference of 25°–50° C. (about 40° C. at the crossover point) in favor of Catalyst C of the invention.

Comparing results for Catalyst C and Catalyst R at 275° C. as μmols of deuterium exchanged per gram of catalyst, results were as follows:

| | |
|---|---|
| Catalyst A | 80 + 10 |
| Catalyst R | 0 |

The catalyst of the invention has significantly greater capability to activate hydrogen.

We claim:

1. A toluene disproportionation catalyst consisting essentially of a molecular sieve having a pore diameter of from about 5 to 8 A, a refractory inorganic oxide and a reduced weak non-framework metal, which metal effects $H_2/D_2$ exchange without effecting methylcyclohexane dehydrogenation at a temperature of between about 300° and 500° C. and wherein at least 75% of the metal is present in the catalyst in a reduced state.

2. The catalyst of claim 1 in which the catalyst comprises between 10 and 30 mass-% carbon as a proportion of the catalyst.

3. The catalyst of claim 1 in which the reduced non-framework metal is chosen from the group consisting of bismuth and rhenium.

4. A toluene disproportionation catalyst consisting essentially of a molecular sieve having a pore diameter of from about 5 to 8 Å, a refractory inorganic oxide and a reduced weak non-framework metal, which metal effects $H_2/D_2$ exchange without effecting methylcyclohexane dehydrogenation at a temperature of between about 300° and 500° C. and wherein at least 90% of the metal is present in the catalyst in a reduced state.

5. A toluene disproportionation catalyst consisting essentiallly of a molecular sieve having a pore diameter of from about 5 to 8 Å, an amorphous refractory inorganic binder comprising an alumino-phosphate and a reduced weak non-framework metal capable of effecting $H_2/D_2$ exchange but not methylcyclohexane dehydrogenation at temperatures between 300° and 500° C. and wherein at least 50% of the metal is present in a reduced state.

6. A toluene disproportionation catalyst consisting essentially of a molecular sieve having a pore diameter of from about 5 to about 8 Å, an amorphous refractory inorganic binder comprising an alumino-phosphate and a reduced weak non-framework metal capable of effecting $H_2/D_2$ exchange but not methylcyclohexane dehydrogenation at temperatures between 300° and 500° C., and wherein at least 75% of the metal is present in a reduced state.

7. The catalyst of claim 6 wherein the metal is chosen from the group consisting of bismuth and rhenium.

* * * * *